US00PP19962P2

(12) United States Plant Patent
Klemm

(10) Patent No.: US PP19,962 P2
(45) Date of Patent: Apr. 28, 2009

(54) ***BRACTEANTHA* PLANT NAMED 'KLEBB07391'**

(50) Latin Name: *Bracteantha bracteata*
Varietal Denomination: KLEBB07391

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/079,381

(22) Filed: Mar. 26, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—Jondle & Associates, P.C.

(57) ABSTRACT

A new cultivar of *Bracteantha* particularly characterized by a medium-early flowering response, shiny, dark-orange flowers, a rounded, bushy, upright plant habit with good growth and branching and a good production of cuttings, is disclosed.

1 Drawing Sheet

Genus and species: *Bracteantha bracteata.*
Variety denomination: 'KLEBB07391'.

BACKGROUND OF THE NEW PLANT

The present invention comprises a new and distinct cultivar of *Bracteantha,* botanically known as *Bracteantha bracteata,* and hereinafter referred to by the cultivar name 'KLEBB07391'. 'KLEBB07391' was discovered as a seedling resulting from a cross in summer 2003 in Stuttgart, Germany between the proprietary female *Bracteantha* parent, 'BV 123' (unpatented) and the male parent, an unnamed typical individual plant of *Bracteantha* (unpatented). A single plant selection was subsequently chosen for further evaluation and for asexual propagation.

The new cultivar was created in 2003 in Stuttgart, Germany and has been asexually reproduced repeatedly by vegetative cuttings in Stuttgart, Germany over a three and one-half-year period. 'KLEBB07391' has been found to retain its distinctive characteristics through successive asexual propagations.

SUMMARY OF THE INVENTION

The following are the most outstanding and distinguishing characteristics of this new cultivar when grown under normal commercial practices in a greenhouse in Stuttgart, Germany.

1. A medium-early flowering response;
2. Shiny, dark-orange flowers;
3. A rounded, bushy, upright plant habit with good growth and branching; and
4. Good production of cuttings.

DESCRIPTION OF THE PHOTOGRAPH

This new *Bracteantha* plant is illustrated by the accompanying photograph which shows a close-up of the mature flower; the colors shown are as true as can be reasonably obtained by conventional photographic procedures. The photograph is of a plant about 4-months old and grown from rooted cuttings in a 12-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEBB07391'. The data which define these characteristics were collected from asexual reproductions carried out in Stuttgart, Germany. The plant history was taken on 3-month old plants in 12-cm pots that were pinched once approximately 12 days after planting and grown in a greenhouse in February through May. The color readings were determined under natural light. Color references are to the RHS Colour Chart of The Royal Horticultural Society of London (RHS) (2001).

DESCRIPTION OF THE NEW PLANT

Classification:
- *Family.*—Asteraceae.
- *Genus and species.*—*Bracteantha bracteata.*

Parentage:
- *Female parent.*—The proprietary *Bracteantha* parent, 'BV 123' (unpatented).
- *Male parent.*—An unnamed typical individual plant of *Bracteantha* (unpatented).

Plant:
- *Form.*—Rounded, bushy.
- *Growth habit.*—Upright.
- *Propagation type.*—Vegetative cuttings.
- *Height from soil level to top of plant plane.*—32.0 cm.
- *Diameter* (*area of spread*).—30.0 cm.
- *Time to initiate roots.*—6 days during summer and 8 days during winter.
- *Time to produce a rooted cutting.*—18 days.
- *Root description and habit.*—Dense, freely branching, white, medium-thickness and fibrous texture.
- *Time to produce a finished plant.*—74 days.

Branches:
- *Type.*—Lateral branches.
- *Quantity per plant.*—7 to 12 after pinching.
- *Length.*—3.0 cm to 8.0 cm.

*Diameter.*—2.0 cm to 3.0 cm.
*Internode length.*—0.2 cm to 1.0 cm.
*Aspect.*—Flat.
*Strength.*—Moderate.
*Texture.*—Smooth.
*Color.*—RHS 137C.

Leaves:
*Arrangement and type.*—Alternate.
*Length.*—5.0 cm to 12.0 cm.
*Width.*—1.0 cm to 2.5 cm.
*Shape.*—Elliptical.
*Apex.*—Acute.
*Base.*—Attenuate.
*Margin.*—Entire.
*Texture* (*both upper and lower surface*).—Smooth.
*Venation pattern.*—Pinnate.
*Venation color* (*both upper and lower surface*).—RHS 137D.
*Color.*—Upper surface (both immature and mature): RHS 137B. Lower surface (both immature and mature): RHS 137C.
*Petiole.*—Absent.

Inflorescence:
*Appearance.*—Single and dichasium.
*Flowering habit and timing.*—Continuous from spring to fall.
*Quantity of inflorescences on the plant.*—5 to 10.
*Fragrance.*—Absent.
*Lastingness of inflorescences on the plant.*—About 14 days.
*Diameter.*—6.0 cm to 8.0 cm.
*Depth* (*height*).—5.0 cm to 7.0 cm.
*Receptacle diameter.*—2.0 cm to 4.0 cm.
*Receptacle height.*—1.5 cm to 2.0 cm.

Bud:
*Height.*—0.5 cm to 1.5 cm.
*Diameter.*—0.5 cm to 1.0 cm.
*Shape.*—Elliptic.
*Color.*—RHS 178A.

Involucral bracts:
*Shape.*—Elliptic.
*Length, largest bracts.*—1.5 cm to 3.0 cm.
*Width, largest bracts.*—0.5 cm to 0.8 cm.
*Apex.*—Acute.
*Base.*—Attenuate.
*Margin.*—Entire.
*Texture.*—Rough.
*Color* (*when opening and when full opened*).—Upper surface: RHS 137A. Lower surface: RHS 137C.

Disc florets:
*Arrangement.*—Massed in the center of the receptacle.
*Shape.*—Tubular.
*Apex.*—Obtuse.
*Length.*—0.2 cm.
*Diameter, apex.*—0.05 cm.
*Diameter, base.*—0.05 cm.
*Number of disc florets per inflorescence.*—Greater than 50.
*Color.*—Immature: Yellow. Mature: Yellow. Apex: Yellow. Mid-section: Yellow. Base: Yellow.

Phyllaries:
*Quantity per inflorescence.*—8 to 10.
*Length.*—0.4 cm.
*Width..*—0.4 cm.
*Shape.*—Elliptic to round.
*Apex.*—Acute.
*Base.*—Obtuse.
*Margin.*—Entire.
*Texture* (*both the upper and lower surfaces*).—Smooth.
*Color.*—Upper surface: RHS 137A. Lower surface: RHS 137A.

Peduncles:
*Length.*—5.0 cm to 8.0 cm.
*Diameter.*—0.2 cm to 0.3 cm.
*Strength.*—Moderate.
*Aspect.*—Erect.
*Texture.*—Rough.
*Color.*—RHS 137D.

Reproductive organs: Unable to determine reproductive organs due to small size.

Fruit and seed set: None observed.

Disease and insect resistance: Not observed.

COMPARISON WITH PARENTAL AND COMMERCIAL CULTIVARS

'KLEBB07391' differs from the female parent, the proprietary *Bracteantha* 'BV 123' (unpatented) in that 'KLEBB07391' has a medium growth habit, has shiny dark-orange flowers and has a medium-early flowering response, while 'BV 123' has a strong plant habit, has yellow-orange flowers and has an early flowering response.

'KLEBB07391' differs from the commercial comparison variety 'KLEBA04086' (U.S. Plant Pat. No. 17,919) in that 'KLEBB07391' has smaller leaves, better branching and an earlier flowering response than 'KLEBA04086'. Additionally, 'KLEBB07391' has shiny dark-orange flowers and is more tolerant to diseases, while 'KLEBA04086' has bronze-colored flowers and is less tolerant to diseases (i.e., is sensitive to *Botrytis*).

I claim:

1. A new and distinct cultivar of *Bracteantha* plant as shown and described herein.

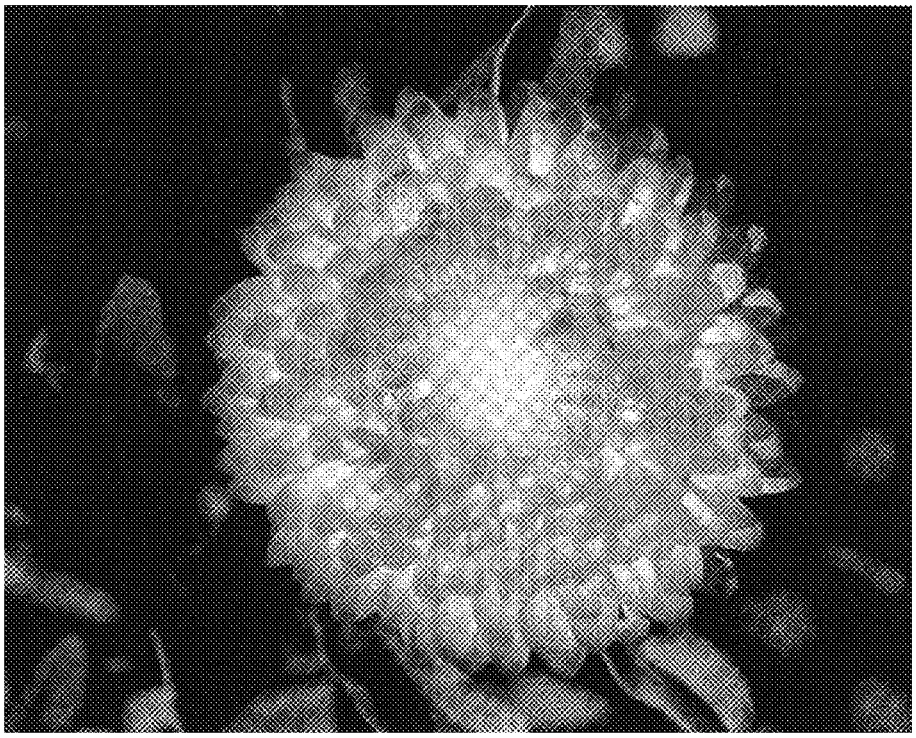

* * * * *